United States Patent [19]

Mynatt

[11] 4,320,198
[45] Mar. 16, 1982

[54] FIBER PRODUCTION FROM CONTINUOUS CULTIVATION OF MICRO-ORGANISMS

[76] Inventor: Roy L. Mynatt, 1929 Plymouth Rd., #1014, Ann Arbor, Mich. 48105

[21] Appl. No.: 84,786

[22] Filed: Oct. 15, 1979

Related U.S. Application Data

[63] Continuation-in-part of Ser. No. 64,387, Aug. 8, 1979, abandoned.

[51] Int. Cl.$^3$ .............................................. C12P 19/04
[52] U.S. Cl. .................... 435/101; 435/287; 435/823; 162/99
[58] Field of Search ............... 435/101, 823, 911, 287, 435/284, 285, 286, 261, 310; 162/157 R, 146, 99

[56] References Cited

U.S. PATENT DOCUMENTS 4,025,394 5/1977 Young .................................. 435/261
4,153,510 5/1979 Messing ................................ 435/176

FOREIGN PATENT DOCUMENTS 580595 9/1946 United Kingdom ................ 435/101

OTHER PUBLICATIONS

Gaudy et al., *Appl. Microbiol.* 9:580–584, 1961.
Nature, vol. 159, Jan. 11, 1947, pp. 64–65.

*Primary Examiner*—William F. Smith
*Attorney, Agent, or Firm*—James M. Deimen

[57] ABSTRACT

An apparatus and process for the production of polysaccharide (cellulose) fibers for use in paper manufacturing. The fibers are produced by the harvesting of the liberated products of continuous micro-organism cultivation. In the preferred embodiment a suitable micro-organism such as *Sphaerotilus natans* is grown on a pitted metallic plate supplied with a flowing nutrient substrate. With abundant pellicle growth the nutrient flow is halted temporarily while a blade passes over the plate harvesting the pellicle growth and depositing the harvest products onto a sluice conveyor. Conventional paper stock washers inundate the blade and wash the products onto the sluice conveyor. The blade is retracted and the nutrient flow restored until the pellicle growth again becomes abundant. The harvest products are then further processed to remove undesirable noncellulosic materials depending upon the particular micro-organisms used.

13 Claims, 3 Drawing Figures

FIBER PRODUCTION FROM CONTINUOUS CULTIVATION OF MICRO-ORGANISMS

BACKGROUND OF THE INVENTION

This application is a continuation-in-part of application Ser. No. 064,387, filed Aug. 8, 1979, abandoned.

The field of the invention pertains to the production of cellulose fibers for use in the manufacture of paper. Vast quantities of pulp wood are required for the production of paper and paper products. The harvesting of wood, transportation and processing to minute cellulosic fibers suitable for paper making are expensive in energy and resources.

Minute cellulose fibers can be produced by cultivation of suitable bacterial and fungal micro-organisms. Continuous cultivation of micro-organisms in microbiology laboratories has been employed principally for the measurement of respiration rates, substrate nutrient consumption and growth rates of micro-organisms. Such continuous cultivation is discussed in the following two papers:

"Continuous Phased Culture—Experimental Technique" P. S. S. Dawson, MICROBIAL GROWTH, Ed. P. P. S. Dawson, Benchmark Papers in Microbiology, 1974

"Steady State Enrichment Cultures of Bacteria" E. J. Ordal, F. E. Palmer, CONTINUOUS CULTIVATION OF MICRO ORGANISMS, PROCEEDINGS OF THE SECOND SYMPOSIUM, Prague, June 18-23, 1962, Eds. Malek, Beran & Hospodka, Academic Press, N.Y.

In addition, the use of very fine cellulosic materials in the manufacture of paper is disclosed in U.S. Pat. Nos. 3,364,101 and 4,104,115.

SUMMARY OF THE INVENTION

The invention comprises an apparatus and process for the production of polysaccharide (cellulose) fibers for use in paper manufacturing. Rather than from wood, the fibers are harvested already in minute size as the products of continuously cultivated bacterial or fungal micro-organisms grown in a controlled manner. A suitable micro-organism such as Sphaerotilus natans is grown on a pitted metallic plate by supplying a suitable flowing nutrient substrate. With abundant pellicle growth the nutrient flow is temporarily halted and a blade passed over the plate harvesting the pellicle growth and depositing the harvest products onto a sluice conveyor. Upon retraction of the blade the nutrient substrate flow is restored until the harvest cycle is again repeated. The harvest products are then further processed as necessary to remove any undesirable non-cellulosic materials. The particular processing, if necessary, depends upon the particular micro-organism used.

The disclosed process and apparatus thus produces minute cellulosic fibers suitable for paper making. The processing and digesting of wood pulp to produce minute fibers is thereby eliminated with the micro-organism process and apparatus disclosed.

DESCRIPTION OF THE PREFERRED EMBODIMENTS

Figure 1:
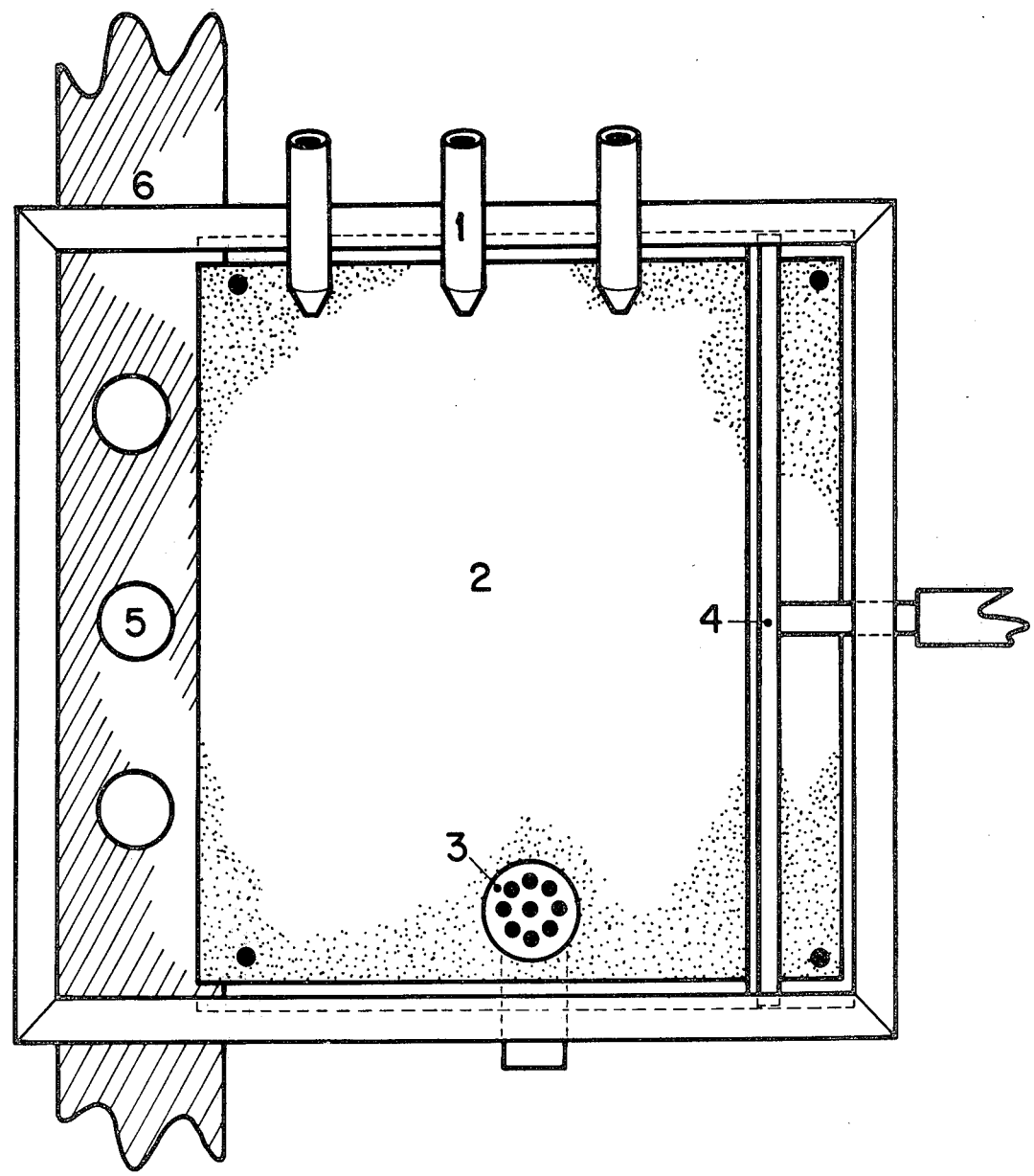
FIG. 1 is a top view of the fiber production apparatus.
Figure 2:
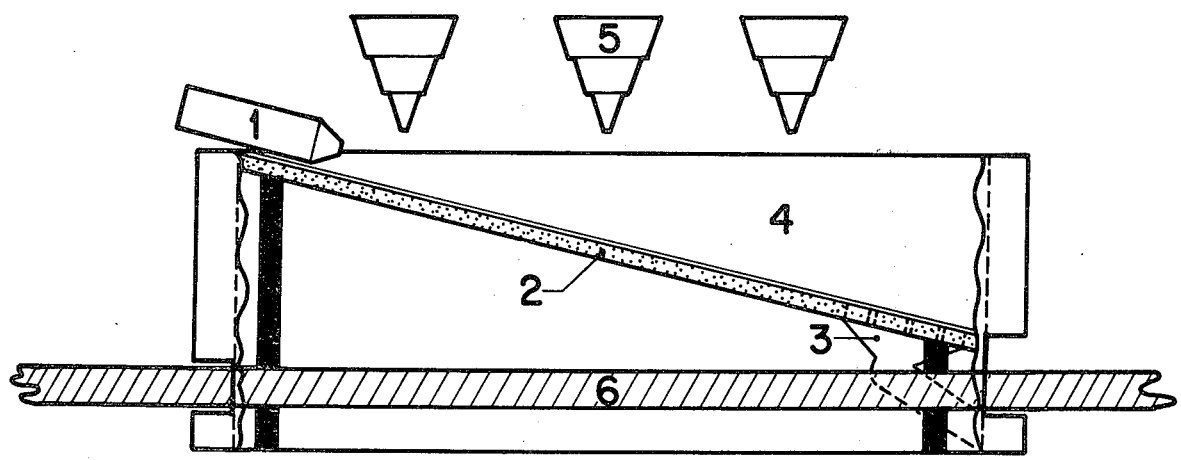
FIG. 2 is a cutaway front view of the fiber production apparatus.
Figure 3:
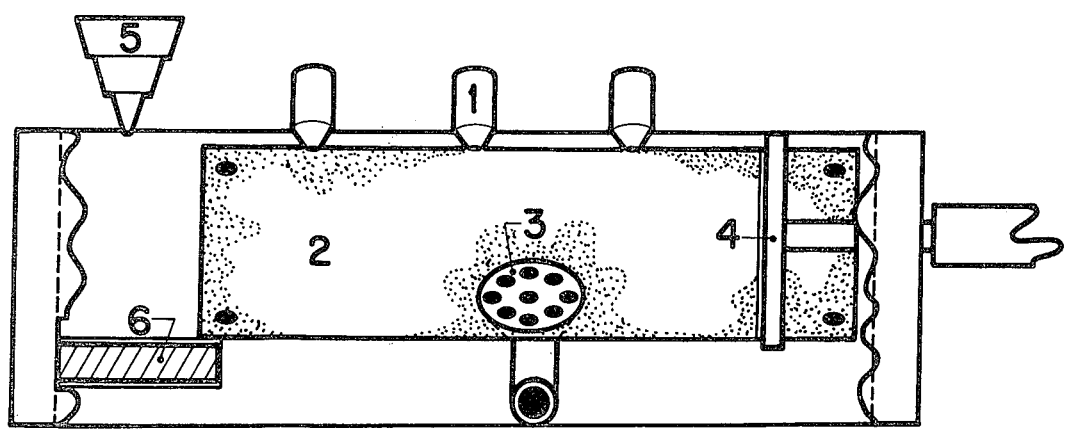
FIG. 3 is a cutaway side view of the fiber production apparatus.

As shown in FIGS. 1, 2 and 3, the apparatus includes a pitted metallic plate 2 extending downwardly from a plurality of nozzles 1. The metallic plate 2 is innoculated with a suitable micro-organism culture as disclosed below. At the lower end of the plate 2 is a drain 3. A suitable nutrient is injected through the nozzles 1 and flows down the plate 2 and into the drain 3. The excess nutrient entering the drain 3 may be mixed with fresh nutrient and recycled through the nozzles 1.

A harvesting blade 4 is shown in a position near full retraction. The blade 4 may be extended across the plate 2 periodically by manual, hydraulic or other suitable means to harvest the fiber growth extending upwardly from the plate 2. The nutrient substrate flow is halted temporarily during the harvesting cycle.

As the blade 4 fully extends beyond the plate 2 and over the sluice conveyor 6, paper stock washers 5 inundate the blade 4 to wash the harvested fibers onto the sluice conveyor. The growth rate of the micro-organisms determines the frequency of harvest. Effectively continuous fiber production can be accomplished by a plurality of the apparatus units at various states of growth.

An example of a suitable micro-organism is the iron bacteria, Sphaerotilus natans. Cell growth of Sphaerotilus natans occurs in long filamentous polysaccharide (cellulose) sheets which as colonies, exhibit well pronounced bulking qualities. The conditions for optimal growth of this organism permits in straightforward fashion continuous cultivation with multiple harvests from the original innoculation of the pitted plate 2.

Using continuous cultivation, conditions can be maintained which will prevent the culture from becoming contaminated by other bacteria. Sphaerotilus natans has low nutrient requirements, good resistance to extreme temperature variations and good tolerance for a high rate of nutrient substrate flow over the plate 2.

A suitable nutrient for continuous cultivation of Sphaerotilus natans in the apparatus disclosed above would comprise:

(1) A nutrient composed of:

| | | |
|---|---|---|
| Bacto-peptone | 1g./liter | water |
| Bacto-dextrose | 1g./liter | " |
| Magnesium sulfate | 1.2g./liter | " |
| Calcium chloride | .05g./liter | " |
| Ferric chloride | .001g./liter | " |
| Bacto-agar | 12.5g./liter | " |

(2) Final pH = 7.0
(3) Nutrient temperature = 25° C. or room temperature
(4) Flow rate = 1.49 ft./sec.

As an alternative, the apparatus above may be modified for the growth of micro-organisms that are non-sesile, such as Acetobacter. A fermenting vat of grain or other liquor at a pH of 5 may be substituted for the pitted plate above and either blade means or a suction (vacuum) means passed over the surface of the vat to extract (harvest) the polysaccharide (cellulose) pellicles.

I claim:

1. A process for the production of cellulose fibers suitable for the manufacture of paper comprising the steps of:

innoculating a pitted plate with a micro-organism adapted to produce abundant cellulosic fibers, supplying a nutrient substrate to the micro-organism sufficient to promote abundant growth of the cellulosic fibers, periodically harvesting the cellulosic fibers produced by the micro-organisms by passing a blade over the plate to shear off the fibers from the micro-organisms, and, treating the fibers to remove any undesirable non-cellulosic materials as required.

2. The process of claim 1 wherein the nutrient substrate flows over the pitted plate.

3. The process of claims 1 or 2 wherein the micro-organism is *Sphaerotilus natans*.

4. A process for the production of cellulosic fibers suitable for the manufacture of paper comprising the steps of:

innoculating a nutrient substrate bath with a micro-organism adapted to produce abundant cellulosic fibers, periodically harvesting the cellulosic fibers produced by the micro-organisms by passing a blade over the surface of the bath to remove the cellulosic fibers from the micro-organisms, supplying additional nutrient to the bath as required, and, treating the fibers to remove any undesireable non-cellulosic materials as required.

5. The process of claim 4 wherein the micro-organism is Acetobacter.

6. Apparatus for the cultivation of micro-organisms that produce cellulosic fiber growth suitable for the manufacture of paper comprising, a pitted plate to support the micro-organism growth, means for flowing a nutrient substrate over the surface of the plate, means for harvesting the fiber growth extending from the pitted plate, the harvesting means comprising a blade adapted to be periodically passed over the surface of the plate to shear off and collect the fiber growth, and, means for conveying the harvested fibers from the harvesting means.

7. The apparatus of claim 6 wherein the means for flowing the substrate include a plurality of nozzles adapted to supply nutrient at one end of the plate, the plate being sloped downwardly therefrom.

8. Apparatus for the cultivation of micro-organisms that produce cellulosic fiber growth suitable for the manufacture of paper comprising, a pitted plate to support the micro-organism growth, means for flowing a nutrient substrate over the surface of the plate, means for harvesting the fiber growth extending from the pitted plate, the harvesting means comprising a blade adapted to be periodically passed over the surface of the plate to shear off and collect the fiber growth, and, a sluice conveyer and washing means to wash the fibers from the blade onto the sluice conveyor.

9. The apparatus of claim 7 wherein the excess nutrient substrate is recycled through the nozzles.

10. The apparatus of claim 6 wherein the pitted plate is innoculated with *Sphaerotilus natans*.

11. The apparatus of claim 8 wherein the means for flowing the substrate include a plurality of nozzles adapted to supply nutrient at one end of the plate, the plate being sloped downwardly therefrom.

12. The apparatus of claim 11 wherein the excess nutrient substrate is recycled through the nozzles.

13. The apparatus of claim 6 wherein the pitted plate is innoculated with *Sphaerotilus natans*.

* * * * *